United States Patent
Carrasco Zanini et al.

(10) Patent No.: US 9,863,919 B2
(45) Date of Patent: Jan. 9, 2018

(54) MODULAR MOBILE INSPECTION VEHICLE

(71) Applicant: Saudi Arabian Oil Company, Dhahran (SA)

(72) Inventors: Pablo Carrasco Zanini, Thuwal (SA); Fadl Abdellatif, Thuwal (SA); Brian Parrott, Dhahran (SA); Hassane Trigui, Thuwal (SA); Sahejad Patel, Thuwal (SA); Ayman Amer, Thuwal (SA); Ali Outa, Thuwal (SA)

(73) Assignee: Saudi Arabian Oil Company, Dhahran (SA)

( * ) Notice: Subject to any disclaimer, the term of this patent is extended or adjusted under 35 U.S.C. 154(b) by 109 days.

(21) Appl. No.: 14/553,876

(22) Filed: Nov. 25, 2014

(65) Prior Publication Data

US 2015/0153312 A1  Jun. 4, 2015

Related U.S. Application Data

(60) Provisional application No. 61/910,328, filed on Nov. 30, 2013.

(51) Int. Cl.
  *G01N 29/265* (2006.01)
  *G01D 5/00* (2006.01)
  (Continued)

(52) U.S. Cl.
  CPC ............ *G01N 29/265* (2013.01); *B25J 5/007* (2013.01); *B60B 19/003* (2013.01);
  (Continued)

(58) Field of Classification Search
  CPC .... G01N 29/28; G01N 29/048; G01N 29/265; G01D 5/00; Y10S 901/44; B60B 19/003; B60B 19/006; B25J 5/007
  (Continued)

(56) References Cited

U.S. PATENT DOCUMENTS

| 4,995,320 A | 2/1991 | Sato et al. |
| 7,210,364 B2 | 5/2007 | Ghorbel et al. |

FOREIGN PATENT DOCUMENTS

| CN | 202 622 792 | 12/2012 |
| CN | 103171640 A | 6/2013 |

(Continued)

OTHER PUBLICATIONS

Tâche, Fabien, et al. "Compact Magnetic Wheeled Robot With High Mobility for Inspecting Complex Shaped Pipe Structures" pp. 1-6. (No Date).

(Continued)

*Primary Examiner* — Daniel S Larkin
(74) *Attorney, Agent, or Firm* — Leason Ellis LLP

(57) ABSTRACT

A modular inspection vehicle having at least first and second motion modules is provided. The first and second motion modules are connected to a chassis. The first motion module includes a first wheel mounted to the chassis. The second motion module includes second wheel mounted to the chassis, the second wheel being at an angle to the first wheel. The vehicle further includes a navigation module configured to collect position data related to the position of the vehicle, an inspection module configured to collect inspection data related to the vehicle's environment, and a communication module configured to transmit and receive data. The vehicle can also include a control module configured to receive the inspection data and associate the inspection data with received position data that corresponds to the inspection data collect at a corresponding position for transmission via the communication module.

31 Claims, 10 Drawing Sheets

(51) Int. Cl.
G01N 29/04 (2006.01)
G01N 29/28 (2006.01)
B25J 5/00 (2006.01)
B60B 19/00 (2006.01)

(52) U.S. Cl.
CPC .............. B60B 19/006 (2013.01); G01D 5/00 (2013.01); G01N 29/048 (2013.01); G01N 29/28 (2013.01); Y10S 901/44 (2013.01)

(58) Field of Classification Search
USPC ........................................................ 73/865.8
See application file for complete search history.

(56) References Cited

FOREIGN PATENT DOCUMENTS

| CN | 102421571 A | 4/2014 |
|---|---|---|
| JP | 02-120168 | 5/1990 |
| JP | 2000 052282 | 2/2000 |
| KR | 100 855 521 | 9/2008 |
| KR | 2013 0025690 | 3/2013 |
| WO | WO 2014/076806 | 5/2014 |

OTHER PUBLICATIONS

Tâche, Fabien, et al. "Magnebike: A Magnetic Wheeled Robot With High Mobility for Inspecting Complex Shaped Structures". Article first published online: Mar. 6, 2009. pp. 1-33.

"Advanced Environmental Technologies."—Robotics and Inspection Services. 2008. Web. Sep. 2014. <http://www.aettopgun.com/pipe.html>. p. 1 of 1.

"Internal Inspection of Small Pipes; PIPETRON". HiBot Corporation. Grren Innovations Jetro Partnerships. 2005-2012.

"Stainless Steel V-Groove Wheel Casters W-313-SVB-1/2." Hamilton. Web. Sep. 23, 2014. <http://www.hamiltoncaster.com/Casters/Stainless_Steel_Casters/Stainles>. pp. 1-2.

"V Groove Caster Wheels." Caster City. Web. Sep. 23, 2014. <http://www.castercity.com/vgroovew.htm>. pp. 1-3.

"Pipe Handling Conveyors." Cisco-Eagle. Web. Sep. 23, 2014. <http://www.cisco-eagle.com/catalog/c-3278-pipe-handling-conveyor.aspx>. pp. 1-4.

Oddbot. "Service Droid—The Build". Service Droid—The Build Let's Make Robots. Sep. 7, 2013. Web. Oct. 4, 2013. pp. 1-7. <http://letsmakerobots.com/node/38376?page=1>.

"Solid Polymer Converyor Rollers." Power-Core. Web. Sep. 23, 2014. <http://www.intechpower.com/products/solid-polymer-conveyor-rollers-/>. pp. 1-2.

"CamOnWheels." CamOnWheels RSS. Web. Sep. 2014. <http://www.camonwheels.com/>. pp. 1-2.

"HR-MP5 Features." Light Weight Magnetic Climbing Robot. Web. 2010-2014.

Tâche, Fabien, et al. "Adapted Magnetic Wheel Unit for Compact Robots Inspecting Complex Shaped Pipe Structures." Advanced intelligent mechatronics, 2007 IEEE/ASME international conference. pp. 1-6.

"Pipe Wheels." DH Casters Wheels. Web. Sep. 23, 2014. <http://www.dhcasters.com/pipe-wheels-p-1032-1-en.html>. pp. 1-2.

Nishijima, Kentarou et al. "Advanced pipe inspection robot using rotating probe." The Fifteenth International Symposium on Artificial Life and Robotics. Feb. 4-6, 2010. pp. 573-576.

Hernando Leon-Rodriguez et al: "A compact wall-climbing and surface adaptation robot for non-destructive testing", Control, Automation and Systems (ICCAS), 2012 12th International Conference on, IEEE, Oct. 17, 2012 (Oct. 17, 2012), pp. 404-409, XP032291825, ISBN: 978-1-4673-2247-8.

White T et al: "The design and operational performance of a climbing robot used for weld inspection in hazardous environments", Control Applications, 1998. Proceedings of The 1998 IEEE International Conference on Trieste, Italy Sep. 1-4, 1998, New York, NY, USA IEEE, US, vol. 1, Sep. 1, 1998 (Sep. 1, 1998), pp. 451-455, XP010307364, DOI: 10.1109/CCA.1998.728489, ISBN: 978-0-7803-4104-3.

Frederic B Cegla et al: "High-temperature (>500° C.) wall thickness monitoring using dry-coupled ultrasonic waveguide transducers", IEEE Transactions on Ultrasonics, Ferroelectrics and Frequency Control, IEEE, US, vol. 58, No. 1, Jan. 1, 2011 (Jan. 1, 2011), pp. 156-167, XP011343740, ISSN: 0885-3010, DOI: 10.1109/TUFFC.2011.1782.

Sai Igdeok Park et al: "Design of a mobile robot system for automatic integrity evaluation of large size reservoirs and pipelines in industrial fields".

Proceedings of the 2003 IEEE/RSJ International Conference on Intelligent Robots and Systems. (IROS 2003). Las Vegas, NV, Oct. 27-31, 2003; [IEEE/RSJ International Conference on Intelligent Robots and Systems], New York, NY : IEEE, US, vol. 3, Oct. 27, 2003 (Oct. 27, 2003), pp. 2618-2623, XP010675570, DOI: 10.1109/IROS.2003.1249265 ISBN: 978-0-7803-7860-5.

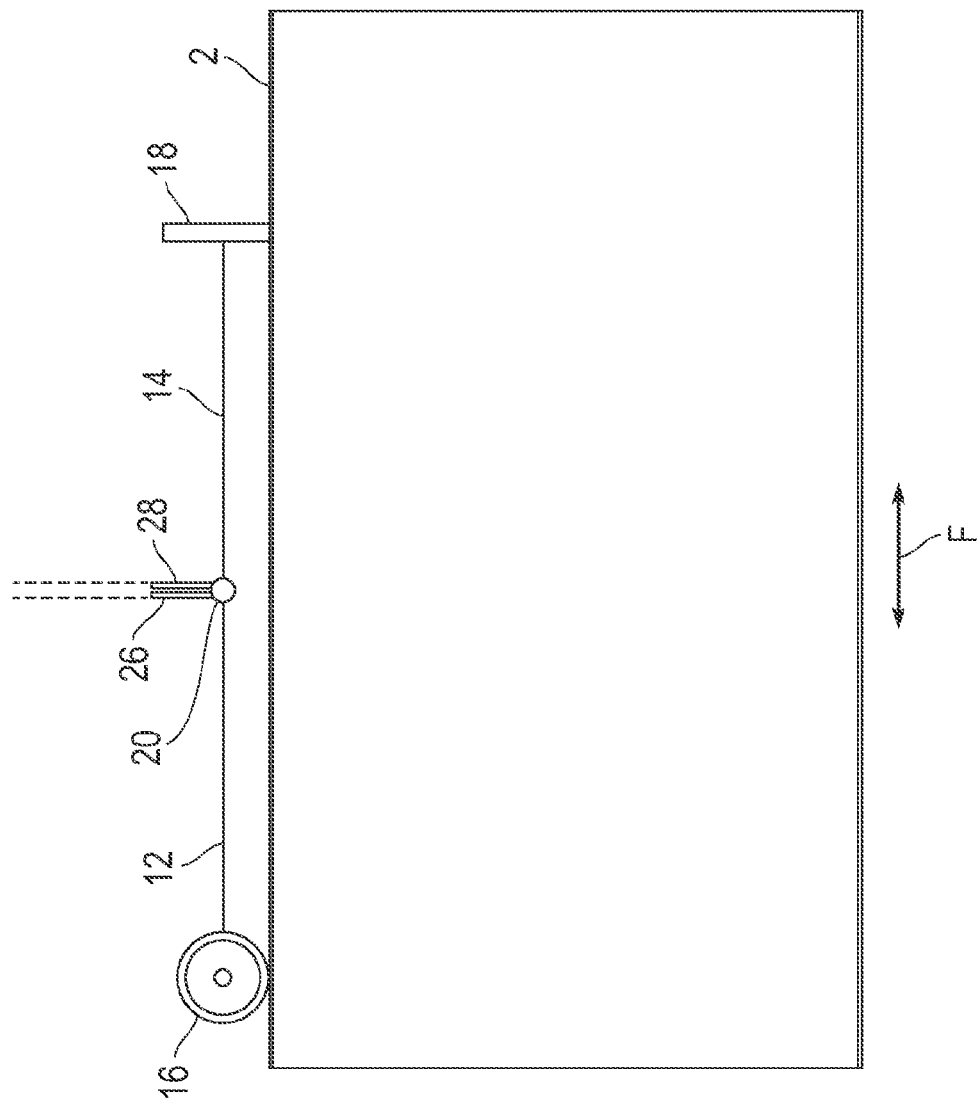

MODULAR MOBILE INSPECTION VEHICLE

CROSS-REFERENCE TO RELATED APPLICATIONS

This application is based on and claims priority to U.S. Provisional Patent Application Ser. No. 61/910,328, filed on Nov. 30, 2013, which is hereby incorporated by reference as if set forth in its entirety herein.

FIELD OF THE INVENTION

The present invention relates to systems and methods for inspection of structures and, in particular, to inspection vehicles.

BACKGROUND

Inspecting hard to reach and inaccessible structures is a costly, time consuming, and potentially dangerous undertaking. In particular, inspecting steel surfaces including elevated pipes, beams, tanks, vessels and other metallic surfaces or structures for flaws, such as corrosion and/or weld failures present challenges. These assets usually either go uninspected for prolonged periods of time or require bundling scaffolding to be able to reach the areas desired to be inspected. The erection and use of scaffolding introduces a safety hazard in the potential for falls, consumes a lot of time and labor to prepare and is also significantly costly.

While certain robotic inspection vehicles are available, these vehicles have many shortcomings. For example, typical robotic inspection vehicles are highly specialized and different vehicles must be purchased for each application. While one vehicle may be able to inspect the walls of a storage tank, that same vehicle is not likely suitable for inspection of pipes. Furthermore, different functions such as visual inspection, ultrasonic inspection and gas sensing require different robots and systems. Further, conventional inspection vehicles are limited in that they typically require a tethered connection which limits their ability to be used to access areas with close-by obstacles (e.g. joints) without getting stuck and having their umbilical cords (tethered) entangled.

The present invention addresses these and other problems.

SUMMARY

According to an aspect of the present invention, there is provided a modular inspection vehicle having a chassis and first and second motion modules. The first motion module includes a first wheel mounted to the chassis for rotation about a first axis. The second motion module includes a second wheel mounted to the chassis, the second wheel being arranged to rotate about a second axis that is at an angle to the first wheel for orthogonal rotation with respect to the rotation direction of the first wheel. The vehicle further includes an inspection module configured to collect inspection data related to the vehicle's environment, a communication module configured to transmit and receive data, and at least one power module configured to provide power to the vehicle and its modules. The vehicle can also include a control module configured to receive the inspection and wherein the control module is configured to prepare the inspection data for transmission via the communication module.

In accordance with a further aspect, a navigation module connected to the chassis is configured to collect position data related to the position of the vehicle.

In accordance with a yet further aspect, the control module is configured to associate the inspection data with received position data that corresponds to the inspection data collected at a corresponding position, and wherein the control module is configured to prepare the associated data for transmission via the communication module.

In accordance with a further aspect, the chassis comprises first and second chassis sections, each coupled to a respective one of the first and second wheels, the sections being connected via a linkage that permits a degree of freedom of movement between the first and second chassis sections.

In accordance with yet a further aspect, the linkage is a hinge.

In accordance with a further, optional aspect, the first wheel is a magnetic driving wheel and the second wheel is magnetic omni-wheel that permits the vehicle to change direction.

In accordance with a further aspect, the magnetic driving wheel and magnetic omni-wheel include high temperature magnets.

In accordance with a further aspect, at least one of the first and second wheels include a magnet.

In accordance with a further aspect, the magnet is a high temperature magnet.

In accordance with a further aspect, the inspection module includes a sensor to detect at least one of a material thickness, fault, and anomaly.

In accordance with a still further aspect, the inspection module includes an ultrasonic transducer.

In accordance with a further aspect, the ultrasonic transducer is a dry coupled probe.

In accordance with a further aspect, the ultrasonic transducer is a wet coupled probe.

In accordance with a still further aspect, the vehicle includes a fluid dispensing module.

In accordance with another aspect, the ultrasonic transducer is a high temperature probe.

In accordance with still further aspect, the ultrasonic transducer is supported by a mount that is biased to maintain the ultrasonic transducer in contact with and normal to a surface to be inspected.

In accordance with another aspect, the vehicle includes a marking module for dispensing a marking material at a desired location.

In accordance with yet another aspect, the vehicle includes a plurality of mounting points that are sized and shaped to receive a plurality of modules.

In accordance with a further aspect, the vehicle includes at least one of a robotic arm module, a gas sensing module, and a temperature sensing module.

In accordance with a further aspect, the power module receives power from onboard batteries.

In accordance with a further aspect, the power module receives power through a tether.

In accordance with a further aspect, a single power module provides power to each of the other modules that require power.

In accordance with a further aspect, a plurality of power modules is provided, wherein a power module is associated with each of the other modules that require power to condition power for each respective module.

In accordance with a yet further aspect, the power modules are incorporated into each of the other modules that require power, respectively.

In accordance with a yet further aspect, the power modules are separate modules that are associated with each of the other modules that require power, respectively.

In accordance with a yet further aspect, the power is supplied by onboard batteries.

In accordance with a yet further aspect, the power is supplied by a tether.

In accordance with a further aspect, the communication module is configured to wirelessly transmit and receive data.

In accordance with a further aspect, the communication module is configured to transmit and receive data via a tether.

BRIEF DESCRIPTION OF THE DRAWINGS

FIG. 2B illustrates a schematic of a modular inspection vehicle on a surface;

DETAILED DESCRIPTION OF CERTAIN EMBODIMENTS

The present invention relates to systems and methods for inspecting structures. According to certain embodiments of the invention, an inspection vehicle is used to accomplish inspection of these structures. The inspection vehicle can use a unique mobility design to climb steel (or other magnetically includible material) surfaces. The robotic vehicle can include an automatically, self-adjusting chassis that adjusts to the geometry of the surface upon which it is traveling. The robotic vehicle can further include one magnetic driving wheel and an orthogonally-mounted (relative to the drive wheel) magnetic omni-wheel for steering. Such a robotic vehicle can include a plurality of inspection modules, such as modules for visual inspection, UT inspection, gas sensing, and robotic arm manipulation. The robotic vehicle can also be wireless and self-contained without the need for tethers or other wired connections to transmit data and/or receive operating commands. The elimination of the tether further increases the mobility of the vehicle and the number of application in which it can be used for inspection. In addition, the vehicle's chassis design and wheel arrangement allows the vehicle to be used on curved surfaces of different diameter without having to change the structure of the vehicle. For example, the same vehicle could be used to inspect an 8 inch diameter pipe and the surface of a large storage tank without having to adjust the structure of the vehicle due to the vehicles versatile and adaptable design.

Figure 1A:
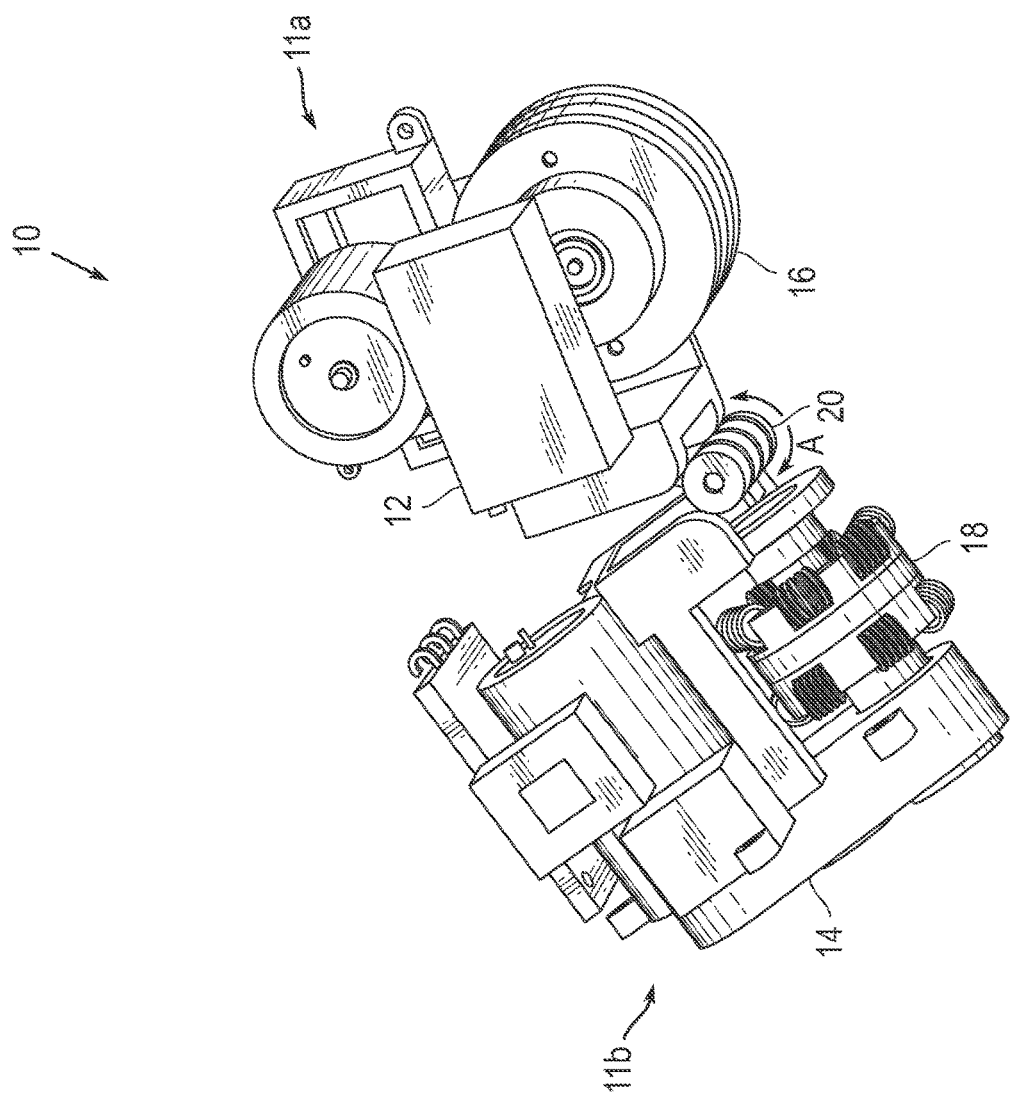
FIG. 1A illustrates a modular inspection vehicle.
Figure 3:
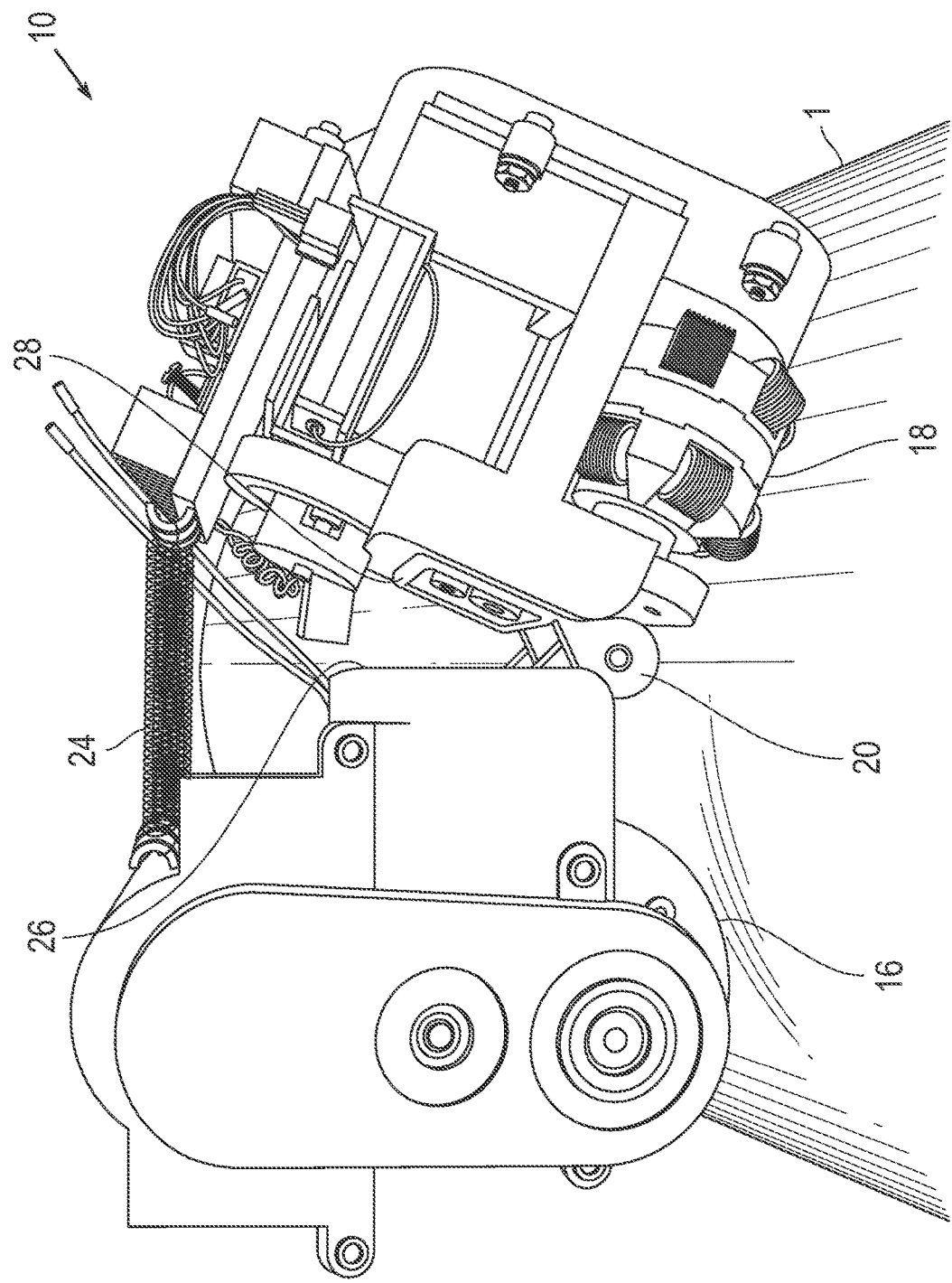
FIG. 3 illustrates side view of a modular inspection vehicle on a curved surface.

Referring to FIGS. 1A and 3, the vehicle 10 utilizes a novel mechanical chassis that comprises of two modules; a driving module 11a and a steering module 11b. The driving module 11a includes a first chassis section 12 and a magnetic drive wheel 16 that drives the vehicle 10 forward and backward. The steering module 11b includes a second chassis section 14 and an orthogonally mounted magnetic omni-wheel 18. The omni-wheel 18 provides active steering and passive sliding (through small rollers) during driving. In other embodiments, a common chassis is provided to which the steering module and drive module are mounted. Common to these embodiments is that the vehicle is capable of supporting various modules that enable the vehicle to perform inspection operations.

The wheels 16 and 18 and/or the chassis sections can include magnets that provide an attractive force between the vehicle and a ferromagnetic/magnetically inducible material (e.g., a material that generates an attractive force in the presence of a magnetic field, such as a steel pipe). The magnets can be selected such that they provide sufficient attractive force to permit the vehicle to travel in vertical and/or inverted positions when traveling along ferromagnetic/magnetically inducible surfaces. In addition, the magnets can be selected to be resistant to extreme temperatures and can also provide a thermal insulating buffer to help isolate the vehicle itself from extreme temperature conditions. The magnetic omni-wheel 18 can have a construction as show in FIGS. 7A-7D, for example, as discussed in more detail below. However, other structural arrangements in which a magnet is incorporated into an omni-wheel can be used.

Referring to FIGS. 7A-7D, an omni-wheel 70 that includes mounting wedges 76 is shown. The omni-wheel 70 includes two hubs 72, a spacer ring 73 disposed between the two hubs, wherein the spacer ring 73 defines a cavity for receiving magnet 74. As discussed above, the spacer ring 73 and the hubs can include indexing notches for alignment of the wheels such that one roller of one hub is oriented such that it is between the gap between two rollers on the other hub. The number of rollers used in relation to the diameter of the hub and the indexing of the hubs reduces the bumpiness in each wheel and provides for a smoother travel. In addition, the spacer 73 is made from a non-ferrous material that does not transfer the magnetic force of the magnet in order to prevent magnetic short circuiting between the two hubs 72. Each hub 72 includes a plurality of rollers 75 that are attached to the hub via mounting wedges 76. The hub 72 includes a plurality of mounting holes 77a that correspond to a mounting hole 77b on each wedge 76 so that the wedges can be connected to the hub (e.g., via a fastener such as a screw, bolt, rivet, pin, etc.). Each wedge includes an axle mounting hole 78 that is sized and shaped to receive axle 79. As cab be seen, rollers 75 are mounted on axle 79 which is supported in the axle mounting hole 78 of wedge 76. The wedge 76 is attached to the hub 72 via mounting holes 77a and 77b. In this arrangement, the wheel can be readily assembled and dissembled. As discussed above, the hubs 72 and the wedges 76 can be made of ferrous material that acts as a flux concentrator. The magnet 74 is orientated such that its poles are directed toward the hubs and wedges which concentrate and direct the flux of the magnet toward the traveling surface. The size and shape of the wedges can be varied such that the distance D between edge of the wedge and the traveling surface is reduced which results in an increase of the magnetic attractive force between the wheel and the surface. The hub, wedges, and the rollers are sized and shaped so that the material of the hubs and wedges are in near contact with the traveling surface as the wheel travels along the surface. It is desirable for the material of the hubs and wedges to be brought in near contact with the traveling surface because the closer the flux concentrating material of the hubs and wedges are brought into contact with the traveling surface, the greater the magnetic attractive force between the wheel and the traveling surface is. However, it is not as desirable for the hub or wedges to actually contact the surface as this increases the drag force of the wheel as it travels along the surface, especially with the wheel is moving perpendicular to the hub (i.e., with the roller rolling in the direction of travel). The outer edge 76a of the wedges 76 can have a concave profile that matches the circumferential profile of the hubs 72. In this way, the wedges 76 can be brought closer to the traveling surface. The concave profile of the wedges also helps to maintain a consistency in the attractive force over a flat edged wedge, for example. This is because the concave shape of the wedge ensures that the distance of between the traveling surface and the wedge is constant and does not change as the wheel rotates (which would occur if the wedge had a straight edge). In this way, the magnetic attractive force between the wheel and the traveling surface can be greatly increased without changing the size of the magnet. Such a construction of a magnetic omni-wheel is particularly useful for use in the hinged robotic vehicle 10. The omni-wheel structure is capable of efficiently directing the force of the magnet in order to maximize the magnetic force that is responsible for holding the vehicle in magnetic purchase with the ferromagnetic traveling surface, especially in vertical and inverted conditions. Thus, smaller magnets can be used, thereby reducing the vehicle size and weight, which in turn increase mobility and power consumption of the vehicle.

Referring again to FIGS. 1A and 3, the first and second chassis sections 12, 14 of the vehicle 10 are connected together via a hinge 20. The hinge 20 can be of several different types, including a knuckle/pin hinge, ball and detent hinge, for example). Other types of structures can be used to provide a degree of freedom between the two chassis sections. For example, a flexible material (e.g., flexible plastic) can be used to connect the two chassis sections together while providing the degree of freedom between the two chassis sections. The hinge 20 provides a degree of freedom of movement between the first and second chassis sections so that they can rotate with respect to each other as indicated by arrow "A". A degree of freedom of movement, which allows for rotation between the first and second chassis sections 12, 14, provides the flexibility of movement for the vehicle to traverse curved surfaces while the drive wheel 16 and omni-wheel 18 remain in contact with and oriented normal to the curved surface 1 (e.g., steel pipe). The degree of freedom can permit movement in both the up and down directions, which can increase the vehicle's ability to traverse both convex surfaces (e.g., outside of a pipe) and concave surfaces (such as the inside surface of a storage tank). The width of the omni-wheel and the magnets that provide attractive force between the wheel and the surface help resist unwanted movement in the up and down directions. The omni-wheel, by its width and its magnets, is biased to be normal to the traveling surface. Accordingly, the omni-wheel itself provides a resistive force to over rotation of the vehicle about the hinge. In addition, the hinge can have other limited degrees of freedom, which can be accomplished by incorporating some play in the hinge design. This play can improve the function of the robot as it moves along particular trajectories that induce a twisting motion between the two chassis sections, such as when the vehicle is traveling in a helical pattern around a pipe.

Figure 1B:
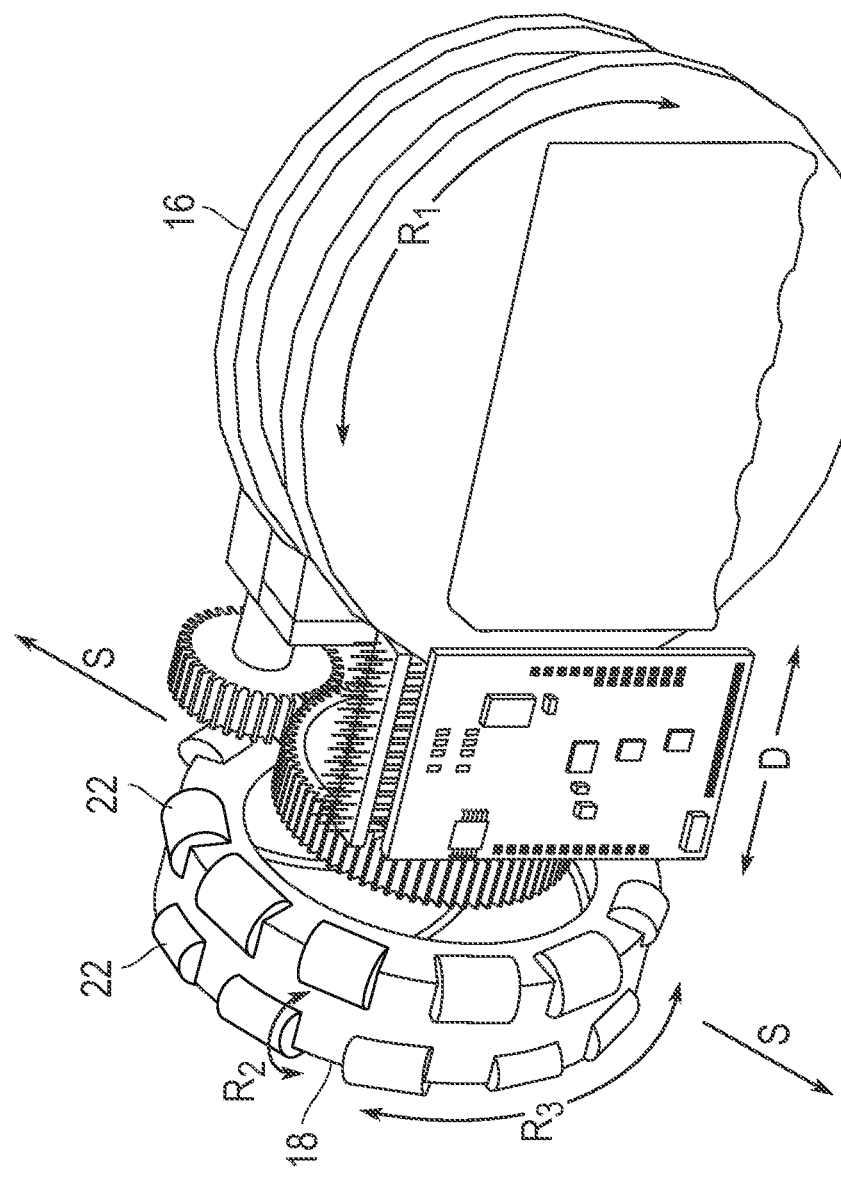
FIG. 1B illustrates additional features of a modular inspection vehicle.

Referring now to FIG. 1B, a simplified sketch shows the orientation of the drive wheel 16 and the omni-wheel 18, without illustrating the hinged chassis. In an embodiment of a robotic vehicle that has a preferred direction of travel that is indicated by arrow "D," the drive wheel 16 of the robotic vehicle 10 rotates about its access in a direction indicated by arrow "R1" in response to a motor that propels the vehicle forward. The axis of rotation of the omni-wheel 18 is nominally oriented perpendicular to the drive wheel 16 (and the wheels are in orthogonal planes), as shown in FIG. 1B. The omni-wheel 18 includes a plurality of rollers 22 that are located around the periphery of the omni-wheel 18. The rollers 22 are mounted on the omni-wheel 18 (via pins or axles, for example) for rotation in the same direction as the drive wheel 16, as indicated by arrow "R2" (i.e., R1 is the same direction as R2). Accordingly, when the drive wheel 16 is driven, the omni-wheel 18 can serve as a follower wheel that is not driven. The rollers 22 passively rotate as the drive wheel 16 is driven, thereby allowing the vehicle to travel in the driven direction as indicated by arrow "D" with the rollers serving the purpose of reducing the friction of the passive omni-wheel 18, at least that is the result when the vehicle 10 is moving along a level surface.

The omni-wheel 18 provides steering, or rotation, to control the robotic vehicle 10. The vehicle 10 can be steered by driving the omni-wheel 18 using the motor mentioned above, or a second motor (neither separately shown) by using conventional linkages between the omni-wheel and the motor. The omni-wheel rotates in a direction indicated by arrow "R3". Rotation of the omni-wheel causes the vehicle to turn or steer in a direction indicated by arrows "S". Controlling the rotation of the omni-wheel 18 allows for steering of the vehicle 10. The hinge 20 is constructed to have minimal to no yield as the omni-wheel is driven in the "S" directions so that the vehicle can be rotated in the direction "S" without the vehicle folding upon itself and so that movement in the "S" direction of the omni-wheel 18 can be correlated with a re-orientation of the drive wheel 16 as a result of the movement transferred to the drive wheel through the hinge 20.

Accordingly, the drive wheel 16 can be controlled to provide forward and rearward movement of the vehicle while the omni-wheel 18 is either a passive, low resistance follower wheel or serving as an active, steering mechanism for the vehicle. The wheels 16, 18 can be activated and driven separately or at the same time to effect different types of steering of the vehicle 10.

The configuration of the wheels of the vehicle provide for excellent mobility and stability while maintaining a relatively small foot print. This permits the robot to fit into small areas and have maneuverability that would be difficult, if not impossible, to achieve with traditional arrangements such as four wheeled vehicles. For example, a vehicle having the described arrangement can be constructed so that it can be effective on surfaces ranging from 8 inches in diameter to completely flat surfaces. The drive wheel 16 provides stability to the vehicle. In particular, the drive wheel includes a strong magnet which creates a pull force between the wheel and a ferromagnetic surface on which the vehicle 10 can be moved, and this structural arrangement assists in resisting tipping of the vehicle. In addition, the drive wheel can have a relatively wide and flat configuration, which further provides stability to the vehicle.

Referring to FIG. 3, the vehicle 10 is shown traversing a curved ferromagnetic surface 1, which, by way of example only, can be a steel pipe. The drive wheel 16 and the omni-wheel 18 can each include a magnet. For example, a magnet can be included in the hub of each of these wheels, or in the case of a double omni-wheel, (as shown, in FIG. 3) between the two hubs. By connecting the drive wheel and the omni-wheel to respective chassis sections, each chassis section is attracted (via the magnets in the wheels) to the ferromagnetic/magnetically inducible material surface (e.g., a material that generates an attractive force in the presence of a magnetic field, such as a steel pipe). Alternatively, or in addition, the chassis sections themselves could include magnets that provided attractive force between each chassis section and the ferromagnetic surface. As such, when the vehicle traverses a curved or uneven surface, each of the chassis sections can be magnetically attracted to the surface. Meanwhile, the hinge 20 enables the chassis sections to rotate relative to one another. By this arrangement, the drive wheel 16 and the omni-wheel 18 maintain contact with and normal to the surface along which the vehicle 10 is traveling. A spring 24 can also extend between the two chassis sections 12, 14 and be connected so as to provide an urging force to assist the sections back to the a position in which the two wheels are located on the same planar surface with approximately zero degrees of rotation between the two chassis sections.

Figure 2A:
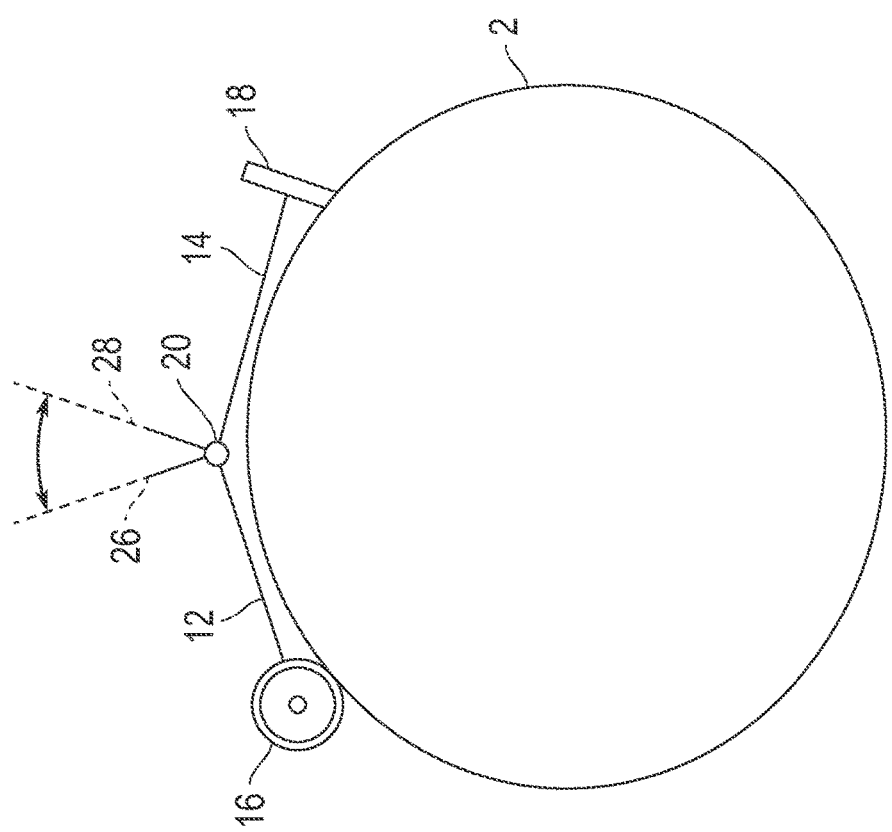
FIG. 2A illustrates a schematic of a modular inspection vehicle on a surface.

Referring now to FIGS. 2A and 2B, a schematic of the robotic vehicle on a curved surface and are on a longitudinal edge of the surface, such as a pipe, respectively. As shown in FIG. 2A, the chassis sections rotate about the hinge 20 so that the wheels maintain contact with the curved surface 2 on which the vehicle is traveling. Without the hinge 20, the chassis would remain in a straight line configuration and one of the wheels could fail to maintain contact the curved surface, or may only be in partial contact with the curved surface (e.g, only an edge of a wheel may maintain contact). Failure of one or two of the wheels to maintain contact with the traveling surface can have significant consequences. First, parts of the wheel such as the perimeter edges can come into contact with the surface which can introduce drag and wear on the parts as the vehicle continues along the surface. Second, that failure can result in a significant drop in the attractive force between the magnets of the chassis and surface. This could have a catastrophic consequence, such as when the vehicle is traversing a vertical or inverted surface, in which the vehicle fails to maintain magnetic purchase with the surface and actually decouples from the surface. Decoupling of the vehicle can result in damage to the vehicle suffered as a result of the fall, present a danger to workers in the area, and/or could result in the vehicle becoming stuck, which could present further problems. As shown in FIG. 2B, the vehicle 10 is disposed on the longitudinal edge of pipe 2. The hinge 20 can include rotation stops 26 and 28. These can be mating surfaces on each of the first and second chassis sections for example. The rotations stops can be positioned to prevent undesired rotation about the hinge 20, or to limit rotation to a set range of degrees, such as when the vehicle is on a flat surface or the two wheels are otherwise on the same plane. For example, the hinges can prevent the vehicle from folding upon itself when on a flat surface such that the hinge joint is dragged on the surface. The stops can also be spaced to allow a limited amount of rotation in both up and down directions. Accordingly, the vehicle can rotate about the hinge to adapt to both concave and convex surfaces. As such, the vehicle can be used on the outside of a pipe (convex surface) as well as in the inside of a tank (concave surface) without structural changes to the vehicle. The degree of freedom can permit movement in both the up and down directions, which can increase the vehicle's ability to traverse both convex surfaces (e.g., outside of a pipe) and concave surfaces (such as a tank surface). The width of the omni-wheel and the magnets that provide attractive force between the wheel and the surface help resist unwanted movement in the up and down directions. The omni-wheel, by its width and its magnets, is biased to be normal to the traveling surface. Accordingly, the omni-wheel itself provides a resistive force to over rotation of the vehicle about the hinge.

In addition, the hinge can have other limited degrees of freedom, which can be accomplished by incorporating some play in the hinge design. This play can improve the function of the robot as it moves along particular trajectories that induce a twisting motion between the two chassis sections, such as when the vehicle is traveling in a helical pattern around a pipe.

As can be seen with further reference to FIGS. 2A and 2B, as the vehicle changes orientation with respect to a curved surface, the angle between the two chassis sections about the hinge 20 changes. When the vehicle is perpendicular to the axis of the curved surface, the angle between the hinge is at its maximum. When the vehicle 10 is disposed on the same curved surface, but the vehicle is oriented parallel to the axis of the curved surface (e.g., parallel to the direction of flow of a pipe) the angle changes. Since the vehicle is located on the ridge of the curved surface, the front and rear wheels are located on the same planar surface. As such, the degree of rotation about the hinge is zero. In this orientation, the angle about the hinge is at its minimum, namely, zero. As the vehicle transitions from an orientation in which the vehicle is perpendicular to the axis of the surface to an orientation in which the vehicle is parallel to the axis of the surface, the angle about the hinge decreases from its maximum to its minimum. By measuring the value of the angle about the hinge, the orientation of the vehicle relative to the curved surface can be determined, as discussed in more detail below.

The value in degrees of this angle is a function of the geometry of the vehicle, the diameter of the curved surface (e.g., pipe) on which the vehicle is located, and orientation of the vehicle with respect to the curved surface. The geometry of the vehicle, which can include the diameter of the wheels and the distance between the wheels and the hinge, are factors that can be measured and known and that remain constant during an inspection performed by the robot. In addition, the diameter of the surface on which the vehicle will be deployed to inspect (e.g., curved pipe) is a factor that can be measured and known and that remains constant during an inspection performed by the robot. In addition, the angle about the hinge in degrees can be measured via a sensor (e.g., using a potentiometer, encoder, strain gauge, the relative difference between two Inertial Measurement Units, one mounted on the driving module and another on the steering module over a short period of time, or other suitable sensors, etc.). Using the known and constant factors associated with the vehicle and the surface, combined with the measured angle about the hinge, the orientation of the vehicle can be calculated. This is particular useful for navigation of the vehicle and can be used as supplement in combination with other navigation systems, such as inertial sensor and/or encoders. The angle between the chassis section provides an indication of the true orientation of the vehicle since the angle is a function of the actual orientation of the vehicle with respect to the curved surface. Thus, the measurement of the angle to determine orientation can be used to correct drift that may occur in other, inferential navigations sensors. Accordingly, if an inertial system indicated an orientation of X degrees and the angle sensor indicated an orientation of X+1 degrees, the angle sensor could be used to correct the drift in the other sensor system in order to ensure more accurate measurements and prevent compounding of the drift.

Figure 5:
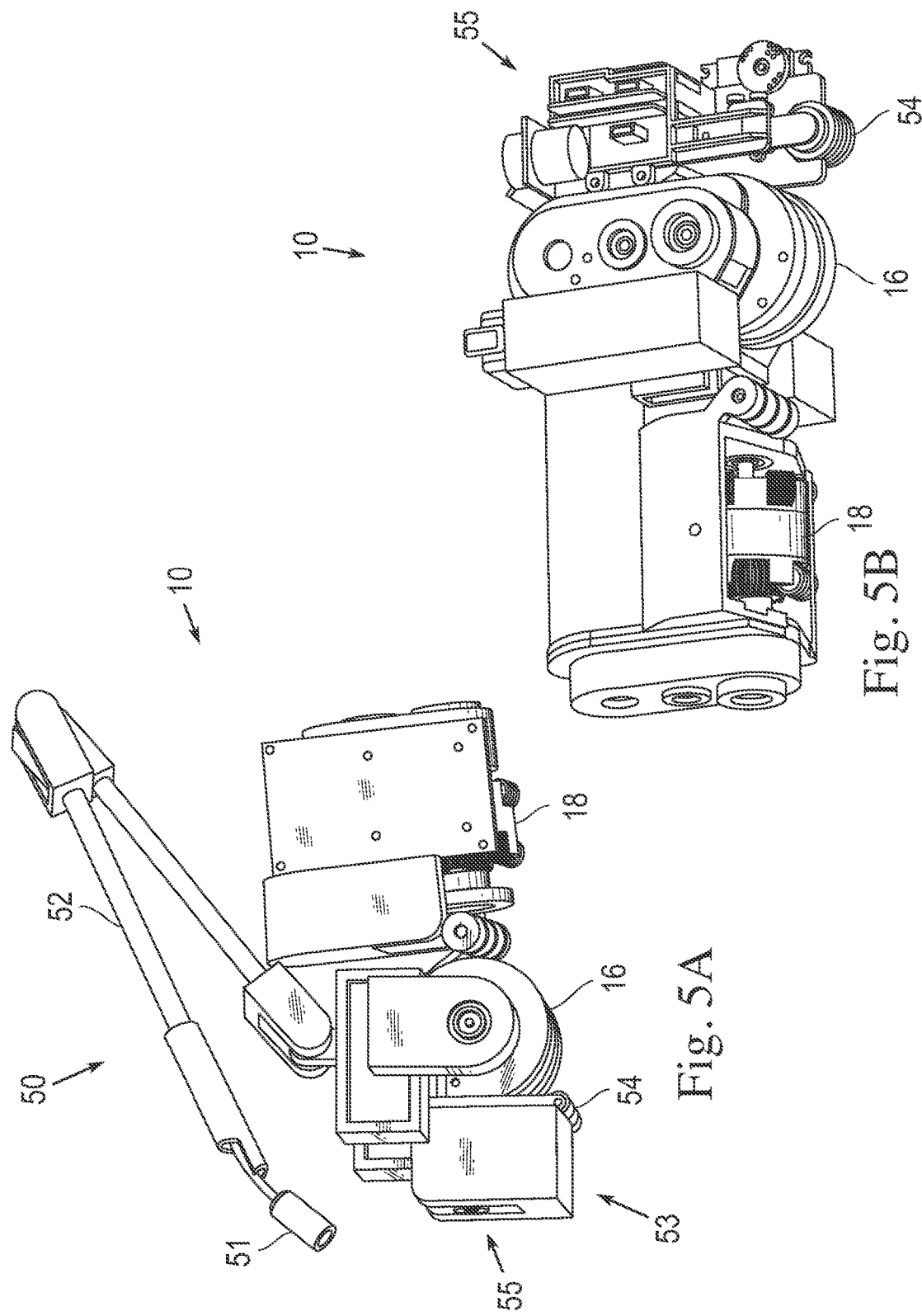
FIG. 5A is a top side view of a modular inspection vehicle having an inspection module and an arm module.
FIG. 5B is a bottom side of a modular inspection vehicle having an inspection module.

The vehicle 10 is able to perform multiple inspection services through the various module options. Referring to FIGS. 5A and 5B, the vehicle is shown with various inspection modules supported by the vehicle. For example, a visual inspection module 50 can in mounted on the vehicle 10 and can include a camera 51 mounted on a controllable boom arm 52. An inspection module can include a sensor that detects corrosion in the inspected surface, such as a metal pipe. The inspection module can detect changes in surface characteristics, chemical changes, and/or changes in thickness of the material. In one example, a corrosion sensor inspection module can include an ultrasonic sensor. An ultrasonic inspection module 53 can also be mounted on the vehicle 10. The ultrasonic inspection module includes a dry coupled ultrasonic probe 54. The use of a dry coupled probe, as opposed to a wet coupled probe that requires a water source, eliminates the need for a tether providing water to the probe thereby increase mobility of the vehicle. The ultrasonic inspection (or ultrasonic testing (UT)) module 53 can include an adaptable mount 55—which is discussed in more detail below—that maintains the ultrasonic probe in a position that is normal to the traveling surface as the vehicle travels along complex trajectories (e.g., helical sweep paths) that are achievable as a result of the vehicle's design. The dry coupled probe 54 provides corrosion mapping/wall thickness of steel surfaces. The probe can detect material thickness, faults, and anomalies in the material, including, but not limited to, corrosion and cracks. A gas sensing module (not shown) can also be mounted on the vehicle. The gas sensing module can measure the concentration of different gases. Adding more modules to achieve additional functions is easy due to its modularity concept. Communication to the vehicle can be achieved through wireless communication links without an umbilical cord or a tether which helps in increasing mobility by avoiding entanglement. Two control modes, which are discussed in more detail below, are available to the operator. At first, the operator has full manual control over the vehicle to drive it up to the area to be inspected. Then, the vehicle can autonomously drive around the pipe in a helical path to provide a full corrosion map of that area using the UT probe.

Figure 6:
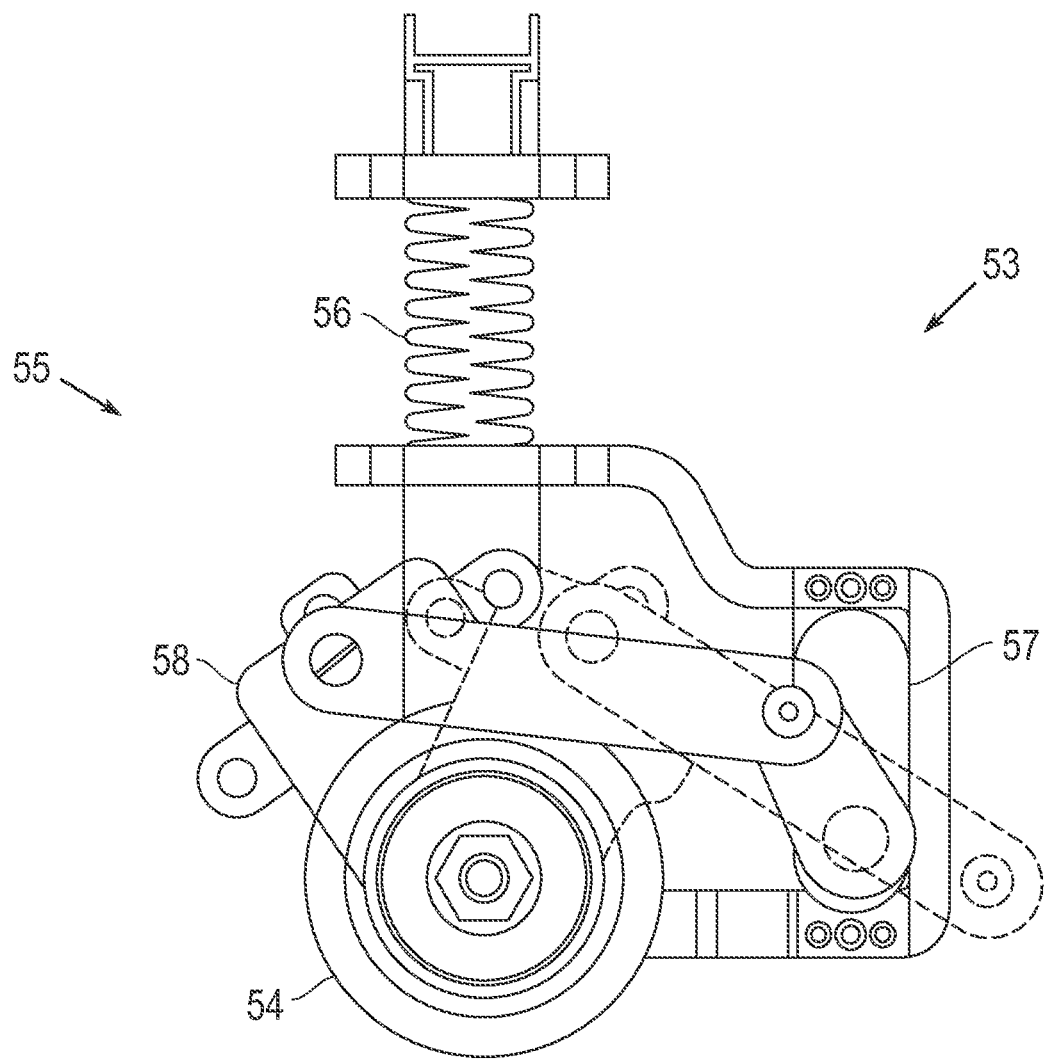
FIG. 6 is a side view of a mount for an inspection probe for a modular inspection vehicle.
Figure 7A:
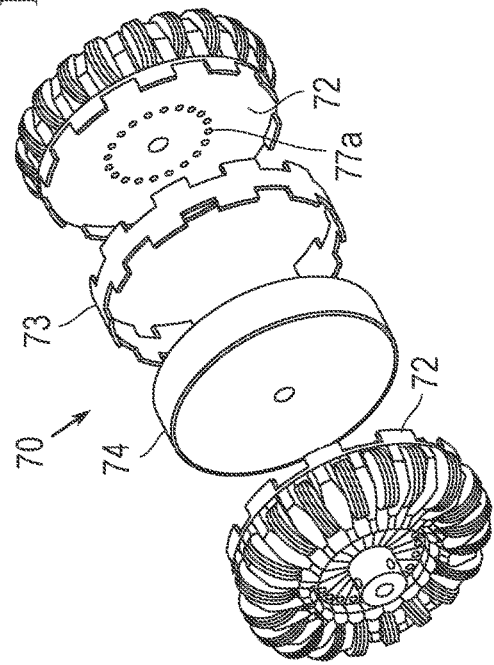
FIGS. 7A-7D illustrate an omni-wheel that can be used with a modular inspection vehicle.
Figure 7B:
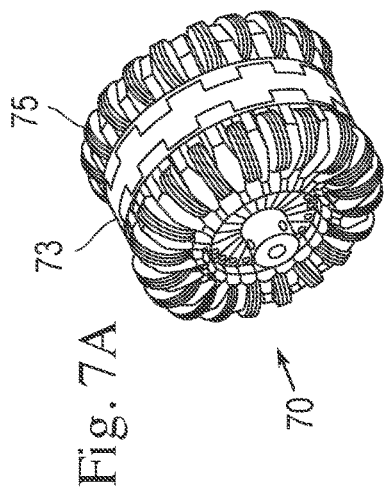
Figure 7C:
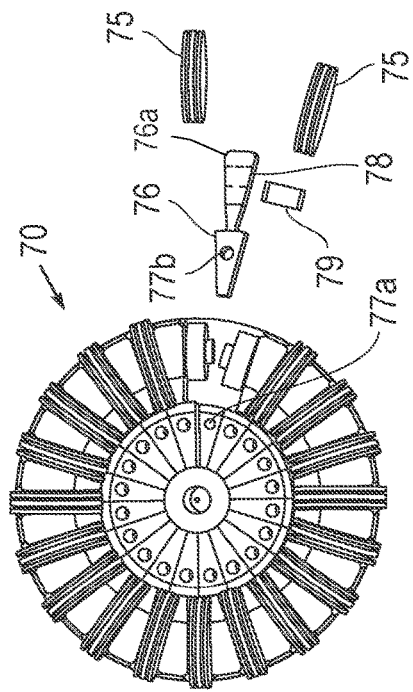
Figure 7D:
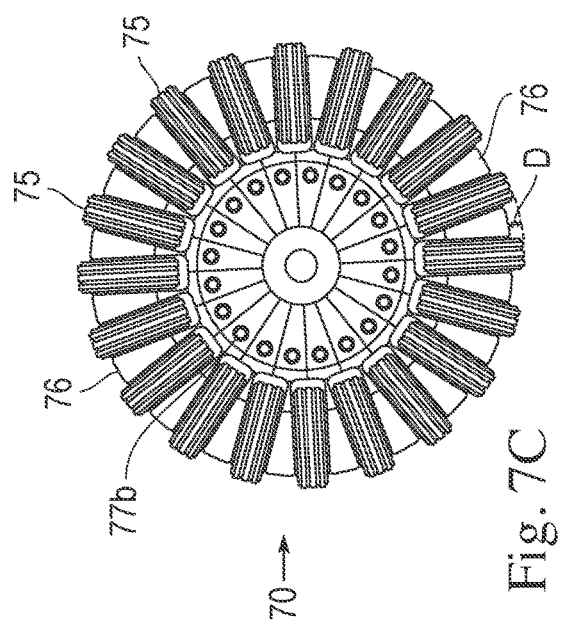

Referring to FIG. 6, the adaptable mount 55 of ultrasonic inspection module 53 is shown. The adaptable mount 55 includes a spring loaded linear actuator 56 that exerts a force upon the probe 54 for maintaining the probe in contact with the surface to be inspected. A four bar linkage system 58 permits the probe 54 to move and adjust to the surface that is being inspected so that the probe can remain normal to the inspection surface for optimal performance of the probe (the dashed and solid lines of the four bar linkage represent two possible positions of adjustment). Two key features distinguish commercially available dry coupled probes over conventional UT probes; it is a dry and/or semi-dry as it does not require the use of water or other couplants except for slight greasing of the wheel to prevent it from wearing out due to any roughness on the inspected surface. Moreover, these wheel probes offers a great advantage over conventional probes and that is the possibility to mount them on a mobile platform to make the inspection task more accurate and easier for the operator. These wheel probes are generally composed of an axle where the transducer is centered inside which then is enclosed by a tire made of synthetic rubber that has acoustic impedance similar to gel or water. Optionally, the probe can also be filled with liquid couplant that transmits the signal to the enclosing rubber. In addition, various other probes can be used, including conventional probes and high temperature probes. In the case that a selected probe requires a "wet" interface with material being inspected, a mechanism for applying a couplant or a transmissive fluid, e.g., a gel or oil, can be provided. The fluid application mechanism can be incorporated into the vehicle design and remotely controlled by the vehicle controllers for dispensing of the couplant. The fluid application module can have a reservoir, an actuator, and a dispensing port, for example. In response to a control signal, the actuator can cause couplant to be moved from the reservoir and dispensed through the dispensing port to the surface being inspected.

The dry coupled probe 54 can be maintained in a position normal to the inspection surface by using a servo motor 57 to control the orientation of the crystal in the UT probe and the spring-loaded linear actuator 56 to apply the appropriate force on the probe during inspection and lift it from the surface while not in use. This mounting mechanism does not use any supporting wheels around the probe to minimize footprint, size and weight even though they can be added if needed. The servo motor 57 is connected to the probe shaft through a four-bar linkage 58 to control its angular displacement with respect to the assembly. It should be noted that the rubber wheel of the probe rolls freely on its shaft and thus an ordinary position servo motor is enough to perform the angular adjustments to achieve normalization on the curved surface. The linear actuator 56 serves at least functions. It lifts the probe off the surface while inspection is not being performed to reduce rubber wear and protect it from lateral dragging. Secondly, during inspection it is used to compress the spring which in turns applies an appropriate compression force on the probe to get the desired UT signal. This mechanism is capable of adjusting on different pipe diameters and also adjusting while moving from longitudinal to helical to radial scanning on the same pipe. For example moving from a flat surface to a pipe (radial scanning) will require an extension from the linear actuator to both lower the probe to make contact with the surface and to compensate the spring compression. The same applies for the differences between longitudinal, helical and radial scanning on the same pipe since these changes are essentially variations in path curvature seen by the probe.

Figure 4:
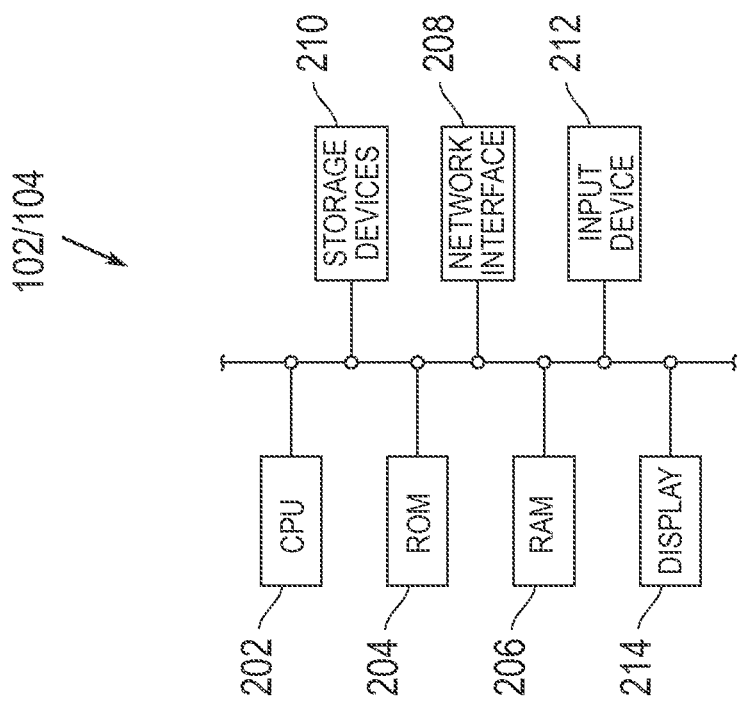
FIG. 4 illustrates a schematic of a subsystem of a modular inspection vehicle.

The method for determining the orientation of the vehicle can be performed by a computer having a processor with memory for executing code. As shown in FIG. 4 the functional elements of an information processor 102 are illustrated, and preferably include one or more central processing units (CPU) 202 used to execute software code in order to control the operation of information processor 102, read only memory (ROM) 204, random access memory (RAM) 206, one or more network interfaces 208 to transmit and receive data to and from other computing devices across a communication network, storage devices 210 such as a hard disk drive, flash memory, CD-ROM or DVD drive for storing program code, databases and application code, one or more input devices 212 such as a keyboard, mouse, track ball and the like, and a display 214. The various components of information processor 102 need not be physically contained within the same chassis or even located in a single location. For example, as explained above with respect to databases which can reside on storage device 210, storage device 210 may be located at a site which is remote from the remaining elements of information processors 102, and may even be connected to CPU 202 across communication network 106 via network interface 208. For example, data processing can be performed using processors located on board the robot and transmitted to a remote computer terminal.

The functional elements shown in FIG. 4 (designated by reference numbers 202-214) are preferably the same categories of functional elements preferably present in user computing device 104. However, not all elements need be present, for example, storage devices in the case of PDAs, and the capacities of the various elements are arranged to accommodate expected user demand. For example, CPU 202 in user computing device 104 may be of a smaller capacity than CPU 202 as present in information processor 102. Similarly, it is likely that information processor 102 will include storage devices 210 of a much higher capacity than storage devices 210 present in workstation 104. Of course, one of ordinary skill in the art will understand that the capacities of the functional elements can be adjusted as needed.

For example, sensors measuring the angle of the hinge can provide electrical input signals to the processor. Such signals can undergo analog or digital signal processing before being inputted to the processor 202, such as by a pre-processing module implemented as computer code executing in the processor 202 or in a separate analog-to-digital converter (ADC). Such a module can receive output from an analog-to-digital converter, which in turn receives signals from a sensor, e.g., a strain gauge. The calculations used to determine the orientation of the vehicle can be performed by processors located on board the robotic vehicle. Alternatively, or in addition, sensed data can be transmitted (e.g., through wireless communications) to a remote processor (e.g., a field laptop computer, smartphone, tablet, etc.) to perform the processing to determine the orientation and location of the vehicle.

Figure 8:
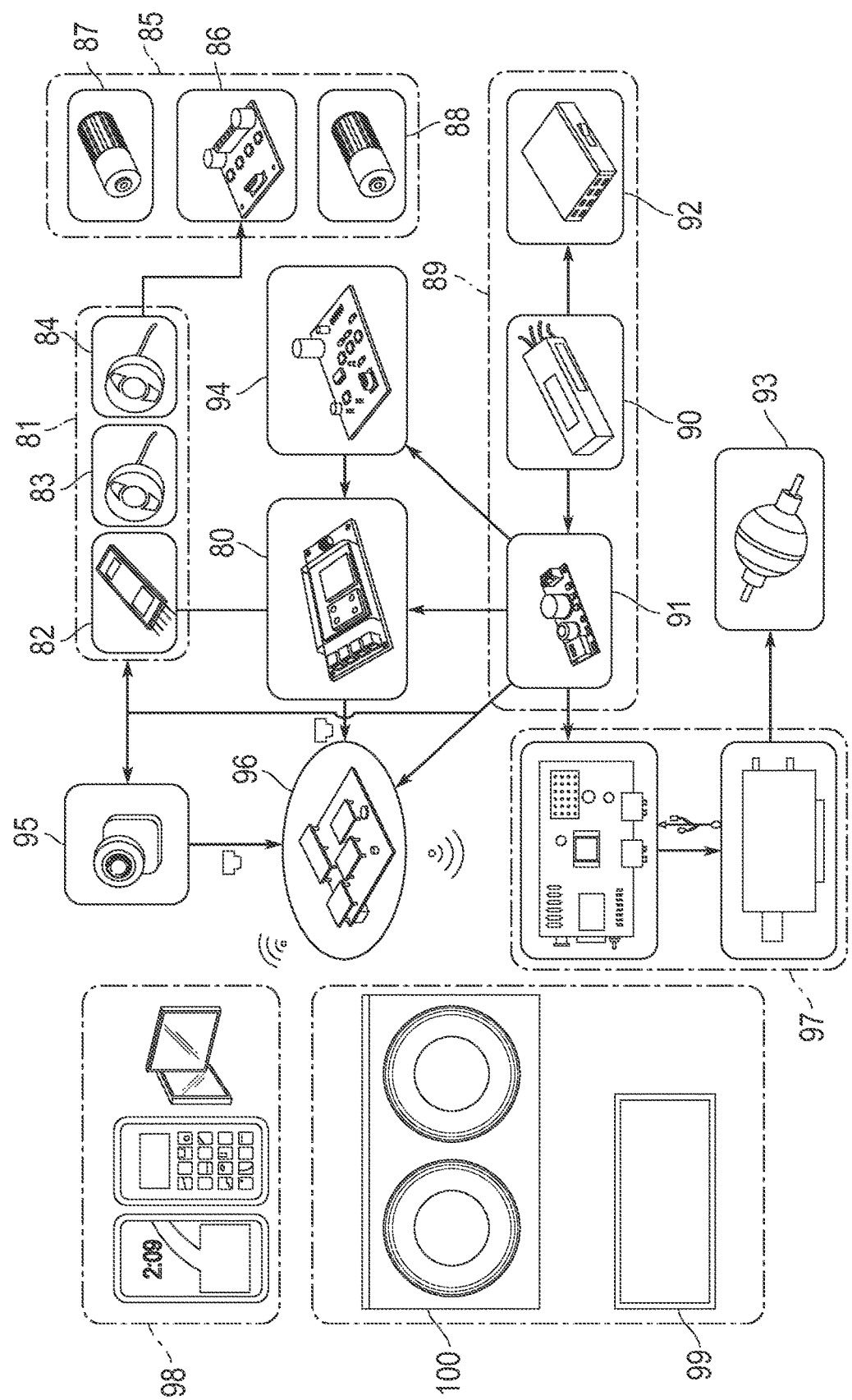
FIG. 8 is a schematic view of a modular inspection vehicle and various subsystems.

FIG. 8 provides a block diagram illustration of an exemplary control system for the vehicle 10. A microcontroller 80 is provided that stores software code for controlling the operation of the vehicle and sending instructions to the various inspection modules. The vehicle includes a navigation system 81. The navigation system 81 can include an inertial system 82 that can include accelerometers and gyros as a means of determining the position of the vehicle. In addition, the navigation system may include encoders 83 for sensing the number of rotations of the driving wheel and/or the steering wheel. The navigation system can further include a sensor for measuring the angle between the two chassis section of the robot to determine the orientation of the vehicle with respect to a curved surface, as discussed above.

Data collected from the navigation system 81 can be analyzed by the microcontroller 80 in order to generate instructions to control the motion system 85. The motion system 85 can include a motion controller module 86 that receives instructions from the microcontroller 80 and in turn controls the operation of the driving motor 87 and steering motor 88 in order to control the trajectory of the vehicle.

The vehicle 10 can include a power system 89 that include a battery 90. A low voltage converter 91 (e.g., 5V DC) can provide power to the electronics of the system (e.g., the microcontroller, wireless communication system, sensor modules, etc.). A second converter 92 can be used to provide higher voltages (e.g., 12V DC) to other systems of the vehicle (e.g., motors). As such, the vehicle power module can include either rechargeable or non-rechargeable batteries. Alternatively, in a configuration that includes a tether, the power module can receive power from an outside source from the tether. A single power module can be provided that conditions the power for all the other modules on the vehicle that require power. A plurality of power modules can also be provided such that each module that requires power can have a power module associated with it so that each module can condition and deliver power to its respective module. The power modules can also be integrated into each of the modules that require the power, for example.

The vehicle 10 can include a plurality of inspection modules, such as an ultrasonic inspection module 93, a gas detection module 94, a visual inspection camera 95, a robotic arm module (such as controllable boom arm 52, for example), as well as others, for example. Each module can include all the necessary electronics, controls, and eletromechanical elements to operate the module. The inspection modules can communicate with the controller 80 either directly through wired connections or through wireless router 96. The inspection modules can have integrated wireless communication capability. Alternatively, the inspection module can use a transfer module 97 that renders the collected inspection data suitable for wireless transmission.

A remote user interface 98 can be configured to send and receive wireless signals from the vehicle. For example, the user interface 98 can include an application running on a computer, laptop, personal digital assistant, smart phone, tablet, or other suitable device, or can be rendered as a page in a conventional browser application such as Chrome available from Google Inc. Accordingly, the user interface can receive inspection and location data collected by the robot and display that information on a display 99. The user interface can also include a control interface 100 (e.g., a touch screen control interface, or a more traditional physical control interface using buttons and joystick, etc.) to allow the user to wirelessly send instructions to the vehicle to either control its motion and/or its inspection modules.

For example, the microcontroller can receive command instructions from the user interface to advance to a certain location and, once at that location, perform an inspection protocol. Accordingly, the microcontroller can control the motor systems 85 to advance the vehicle to the target location and receive information from the navigation system 81 to confirm the location of the vehicle and adjust the control of the motors to accordingly to arrive at the target location. Once at the target location, the microcontroller can control the motors to move the vehicle in an inspection sweep pattern, which can be a helical pattern around a curved surface (e.g, the exterior of a pipe), for example. While the vehicle is moving in the sweep pattern, the microcontroller can interact with and control the plural inspection modules to perform their respective inspection data collection operations. The microcontroller can then collect the data received from a respective inspection module and associate that inspection data with data collected from the navigation system 81. In this way, the microcontroller can associate the inspection data collected with a specific location at which that data was collected. Thus, the microcontroller can create a multimodal data point that can include inspection data and corresponding location data. These multimodal data points can be transmitted wirelessly to the user interface 98 and displayed to the user. The data points can be displayed in the form of a map that shows the location and results of the inspection data. Inspection data from multiple inspection modules can be associated the location data. For example, the map could include UT data, gas detection data, and visual image data collected for each location point over which the vehicle traversed.

The above described vehicle allows for automatic adjustment for curvatures both concave and convex. The degree of freedom introduced inside the chassis between the driving and steering modules allows the vehicles to self-adjust on tight curvatures therefore covering a steel surface, for instance, ranging from flat down to 8" diameter pipes. In contrast, conventional inspection crawlers either work on a specific curvature or have had to be manually adjusted before starting inspection, which means they are fixed to work in one dimension (longitudinally or circumferentially). Having a self-adjusting system allows the vehicle to roam freely on a pipe in any direction since the transition from longitudinal to circumferential driving involves change in the observed curvature by the vehicle. The vehicle can move forward and backward by driving the magnetic drive wheel while the rollers of the omni-wheel allow smooth unrestrained sliding of the omni-wheel. The vehicle can perform a full 360 degree in-place rotation on the pipe surface by operating the steering omni-wheel while pivoting around the driving wheel. Turning right and left while driving is possible by actuating both wheels. A combination of all these driving modes allows the vehicle to perform various intricate maneuvers to avoid obstacles (e.g. joints) and follow helical paths to achieve full pipe coverage during inspection. The in-line placement of the two wheels allows the vehicle to navigate on narrow surfaces such as narrow beams and columns and small diameter pipes. Conventional inspection crawlers have three wheels or more (they don't have this in-line configuration) which make them much wider.

The vehicle 10 is self-contained and is remotely controlled. The vehicle utilizes wireless communication protocols (e.g. WiFi, RF, Zigbee) to receive commands from an operator and send back live video feed and inspection data (e.g. thickness measurement, gas concentration, etc.). A rechargeable battery pack provides power to the robot along with an optional solar panel. Conventional UT inspection crawlers need umbilical cords to provide power and communication since the pulser (UT circuitry that provides the high voltage pulses to the UT probe) is heavy and located on ground requiring a tether to the crawler. The vehicle 10 features an onboard miniature pulser which along with having wireless communication waves the need for an umbilical cord. Eliminating the tether insures improved maneuverability of the robot by avoiding entanglement and the excess weight of the cord which enables accessing hard-to-reach surfaces and elevated pipes unlike conventional crawlers. In certain embodiments in which communication issues are expected, there is a large demand for power, or a need for an external supply of fluid, for example, the vehicle can include a tether. A tether can provide for transmission of communication signals, electrical power, and other elements than can be required by the vehicle, such as additional input data and couplant fluid, for example, in certain applications that demand a tether. For example, the vehicle can include a connection module. The connection module is configured with a suitable connector so that the tether can be connected to the vehicle. Accordingly, as the vehicle moves about during inspection, the tether remains securely connected to the vehicle and moves with it. The tether can be single purpose (e.g., power) or can serve multiple purposes and include multiple components (e.g., power wires, communication wires/fibers, fluid lines, etc.). Accordingly, with the tether connected to the vehicle the other modules can be connected, either directly or indirectly, to the appropriate components of the tether.

Adopting a modular approach in the vehicle 10 improves its ability to carry out a variety of different tasks via multiple detachable modules. These modules can include visual inspection using a camera(s), UT inspection module using a pulser and a dry-coupled probe (or other types of UT probes such as conventional or high temperature probes), gas sensing module, a robotic arm module, for example. This system expands the provided functions of the vehicle without having to unnecessarily carry all the equipment at once. Other potential applications could be fulfilled by developing separate modules to do surface preparation, physically marking the location of defect located as a result inspection process (e.g., via a visual marker such as paint or a physical marker such as a magnetic marker button), coating/painting, minor maintenance/repair, computer-aided damage mechanism detection and security/surveillance. For example, a marking module can include a reservoir of marking material (e.g., paint, dye, or other detectable material) and can receive signals that cause the marking module to dispensing the marking material at the desired location. The marking module can mark locations that have been inspected, damaged, or are in need of critical repair. In addition, the marking module can include several separate reservoirs of differing marking material in order to indicate differing conditions (e.g., one color to indicate that inspection has occurred at a particular location, another color to indicate that a flaw has been detected).

The vehicle module has multiple mounting points allowing different modules to be connected to it. Accordingly, a standardized interface can be used that can provide for physical mounting of the modules as well as electronic coupling for power, control, and data transfer between the module and the other components of the vehicle. The modules can be directly connected to the chassis or indirectly connected to the chassis by, for example, being connected supported by other modules or through additional linkages. Preferable, the steering module containing the magnetic omni-wheel is attached to the back of the driving module to create the omni-wheel vehicle described above. However, different configurations are also attainable by attaching two driving modules side-by-side using two hinges to create a differential steering vehicle that can steer by changing the speed or direction of the two driving wheels. Other configurations include a snake/ring that can be achieved by attaching multiple driving and steering modules either in one line to create a snake-like configuration or in a loop to create a ring-like configuration.

It should be understood that various combination, alternatives and modifications of the present invention could be devised by those skilled in the art. The present invention is intended to embrace all such alternatives, modifications and variances that fall within the scope of the appended claims.

While the invention has been particularly shown and described with reference to a preferred embodiment thereof, it will be understood by those skilled in the art that various changes in form and details may be made therein without departing from the spirit and scope of the invention.

The invention claimed is:
1. A modular inspection vehicle, comprising:
a chassis, wherein the chassis comprises first and second chassis sections, each of the first and second chassis sections are coupled to a respective one of a first wheel and a second wheel, the sections being connected via a linkage that permits a degree of freedom of movement between the first and second chassis sections and maintains the first and second wheels in contact with the surface on which the inspection vehicle is traveling;

a first motion module, the first motion module including:
  the first wheel mounted to the first chassis section for rotation about a first axis, wherein the first wheel is a magnetic driving wheel;
  the second motion module, the second motion module including:
a second wheel mounted to the second chassis section, the second wheel being arranged to rotate about a second axis that is nominally perpendicular to the first wheel for orthogonal rotation with respect to the rotation direction of the first wheel and wherein the second wheel is a magnetic omni-wheel that permits the vehicle to change direction;
an inspection module connected to the chassis configured to collect inspection data related to the vehicle's environment;
a communication module connected to the chassis configured to transmit and receive data;
at least one power module connected to the chassis configured to provide power to the vehicle and its modules; and
a control module connected to the chassis configured to receive the inspection data and wherein the control module is configured to prepare the inspection data for transmission via the communication module.

2. The modular inspection vehicle of claim 1, further comprising a navigation module connected to the chassis and configured to collect position data related to the position of the vehicle.

3. The modular inspection vehicle of claim 2, wherein the control module is configured to associate the inspection data with received position data that corresponds to the inspection data collected at a corresponding position, and wherein the control module is configured to prepare the associated data for transmission via the communication module.

4. The modular inspection vehicle of claim 1, wherein the chassis comprises first and second chassis sections, each coupled to a respective one of the first and second wheels, the sections being connected via a linkage that permits a degree of freedom of movement between the first and second chassis sections.

5. The modular inspection vehicle of claim 4, wherein the linkage is a hinge.

6. The modular inspection vehicle of claim 1, wherein the omni-wheel comprises a plurality of rollers located around a periphery of the omni-wheel, wherein the plurality of rollers are mounted on the omni-wheel for passive rotation in the rotation direction of the driving wheel as the driving wheel is driven, and wherein the omni-wheel is configured to be driven for orthogonal rotation with respect to the rotation direction of the first wheel thereby causing the vehicle to change direction.

7. The modular inspection vehicle of claim 6, wherein the first motion module is a driving module and the second motion module is a steering module, and wherein the first and second wheels can be driven one or more of: separately and at the same time to effect different types of steering of the vehicle.

8. The modular inspection vehicle of claim 1, wherein at least one of the first and second wheels include a magnet.

9. The modular inspection vehicle of claim 8, wherein the magnet is a high temperature magnet.

10. The modular inspection vehicle of claim 1, wherein the inspection module includes a sensor to detect at least one of a material thickness, fault, and anomaly.

11. The modular inspection vehicle of claim 1, wherein the inspection module includes an ultrasonic transducer.

12. The modular inspection vehicle of claim 11, wherein the ultrasonic transducer is a dry coupled probe.

13. The modular inspection vehicle of claim 11, wherein the ultrasonic transducer is a wet coupled probe.

14. The modular inspection vehicle of claim 13, further including a fluid dispensing module.

15. The modular inspection vehicle of claim 11, wherein the ultrasonic transducer is a high temperature probe.

16. The modular inspection vehicle of claim 11, wherein the ultrasonic transducer is supported by a mount that is biased to maintain the ultrasonic transducer in contact with and normal to a surface to be inspected.

17. The modular inspection vehicle of claim 1, further including a marking module configured to dispense a marking material at a desired location.

18. The modular inspection vehicle of claim 1, wherein the vehicle includes a plurality of mounting points that are sized and shaped to receive a plurality of modules.

19. The modular inspection vehicle of claim 1, wherein the vehicle includes at least one of a robotic arm module, a gas sensing module, and a temperature sensing module.

20. The modular inspection vehicle of claim 1, wherein the power module receives power from onboard batteries.

21. The modular inspection vehicle of claim 1, wherein the power module receives power through a tether.

22. The modular inspection vehicle of claim 1, wherein a single power module provides power to each of the other modules that require power.

23. The modular inspection vehicle of claim 1, further comprising a plurality of power modules, wherein a power module is associated with each of the other modules that require power to condition power for each respective module.

24. The modular inspection vehicle of claim 23, wherein the power modules are incorporated into each of the other modules that require power, respectively.

25. The modular inspection vehicle of claim 23, wherein the power modules are separate modules that are associated with each of the other modules that require power, respectively.

26. The modular inspection vehicle of claim 23, wherein the power is supplied by onboard batteries.

27. The modular inspection vehicle of claim 23, wherein the power is supplied by a tether.

28. The modular inspection vehicle of claim 1, wherein the communication module is configured to wirelessly transmit and receive data.

29. The modular inspection vehicle of claim 1, wherein the communication module is configured to transmit and receive data via a tether.

30. A modular inspection vehicle, comprising:
a chassis;
a first motion module, the first motion module including:
  a first wheel mounted to the chassis for rotation about a first axis;
a second motion module, the second motion module including:
  a second wheel mounted to the chassis, the second wheel being arranged to rotate about a second axis that is at an angle to the first wheel for orthogonal rotation with respect to the rotation direction of the first wheel;
an inspection module connected to the chassis configured to collect inspection data related to the vehicle's environment;
a communication module connected to the chassis configured to transmit and receive data;

at least one power module connected to the chassis configured to provide power to the vehicle and its modules;

a control module connected to the chassis configured to receive the inspection data and wherein the control module is configured to prepare the inspection data for transmission via the communication module; and a plurality of power modules, wherein a power module is associated with each of the other modules that require power to condition power for each respective module.

31. The modular inspection vehicle of claim 30, wherein the power modules are separate modules that are associated with each of the other modules that require power, respectively.

* * * * *